United States Patent
Lim et al.

(10) Patent No.: US 7,303,592 B2
(45) Date of Patent: *Dec. 4, 2007

(54) HAIR COLORING COMPOSITIONS FOR USE IN OXIDATIVE HAIR DYEING

(75) Inventors: Mu'lll Lim, West Chester, OH (US); Guiru Zhang, Fairfield, OH (US); Bryan Patrick Murphy, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 335 days.

This patent is subject to a terminal disclaimer.

(21) Appl. No.: 11/077,744

(22) Filed: Mar. 11, 2005

(65) Prior Publication Data

US 2005/0188480 A1 Sep. 1, 2005

Related U.S. Application Data

(63) Continuation-in-part of application No. 10/090,377, filed on Mar. 4, 2002, now Pat. No. 6,887,280.

(51) Int. Cl.
*A61K 7/13* (2006.01)

(52) U.S. Cl. ........................ 8/405; 8/406; 8/408; 8/411; 8/568; 8/570; 8/573; 548/371.4; 548/371.7; 548/373.1; 546/251

(58) Field of Classification Search ............ 8/405, 8/406, 408, 411, 568, 570, 573; 548/371.4, 548/371.7, 373.1; 546/251
See application file for complete search history.

(56) References Cited

U.S. PATENT DOCUMENTS

| 4,900,325 | A | | 2/1990 | Rose | |
|---|---|---|---|---|---|
| 5,061,289 | A | * | 10/1991 | Clausen et al. | 8/405 |
| 5,718,731 | A | | 2/1998 | Loewe | |
| 6,554,871 | B2 | | 4/2003 | Braun | |
| 6,887,280 | B2 | * | 5/2005 | Lim et al. | 8/405 |
| 2003/0196280 | A1 | | 10/2003 | Lim | |

FOREIGN PATENT DOCUMENTS

| DE | 29909427 U | 7/1999 |
|---|---|---|
| DE | 10103160 A | 11/2001 |
| DE | 20206274 U | 8/2002 |
| WO | PCT/US2006/008559 | 9/2006 |

OTHER PUBLICATIONS

STIC Search Report dated Apr. 2, 2007.*

* cited by examiner

*Primary Examiner*—Eisa Elhilo
(74) *Attorney, Agent, or Firm*—Melissa G. Krasovec; Marianne Dressman

(57) ABSTRACT

Hair dyeing compositions are provided which comprise at least one coupler selected from N-aryl-m-phenylenediamine derivatives, 2-substituted N-aryl-m-phenylenediamine derivatives, and N-aryl-m-diaminopyridine derivatives, in combination with and at least one diaminopyrazole primary intermediate.

8 Claims, No Drawings

HAIR COLORING COMPOSITIONS FOR USE IN OXIDATIVE HAIR DYEING

CROSS REFERENCE TO RELATED APPLICATION

This application is a continuation-in-part of prior U.S. application Ser. No. 10/090,377, filed on Mar. 4, 2002 now U.S. Pat. No. 6,887,280.

FIELD OF THE INVENTION

The present invention relates to novel compositions for use in oxidative hair coloring. More particularly, the present invention relates to a hair dyeing composition comprising at least one coupler selected from N-aryl-m-phenylenediamine derivatives, 2-substituted N-aryl-m-phenylenediamine derivatives, and N-aryl-m-diaminopyridine derivatives, in combination with and at least one diaminopyrazole primary intermediate. The present invention also relates to use of these hair dyeing compositions for the coloration of hair.

BACKGROUND OF THE INVENTION

Coloration of hair is a procedure practiced from antiquity employing a variety of means. In modern times, the most extensively used method employed to color hair is to color hair by an oxidative dyeing process employing hair coloring systems utilizing one or more oxidative hair coloring agents in combination with one or more oxidizing agents.

Most commonly a peroxy oxidizing agent is used in combination with one or more oxidative hair coloring agents, generally small molecules capable of diffusing into hair and comprising one or more primary intermediates and one or more couplers. In this procedure, a peroxide material, such as hydrogen peroxide, is employed to activate the small molecules of primary intermediates so that they react with couplers to form larger sized compounds in the hair shaft to color the hair in a variety of shades and colors.

A wide variety of primary intermediates and couplers have been employed in such oxidative hair coloring systems and compositions. Among the primary intermediates employed there may be mentioned p-phenylenediamine, p-toluenediamine, p-aminophenol, 4-amino-3-methylphenol, and as couplers there may be mentioned resorcinol, 2-methylresorcinol, 3-aminophenol, and 5-amino-2-methylphenol. A majority of the shades have been produced with dyes based on p-phenylenediamine.

It is desirable that compositions used for the dyeing or coloration of hair be such as to provide overall color fastness of the dyed hair. Accordingly, the hair dyes with the compositions of the present invention should resist loss of color occasioned by washing, by acid perspiration, and by abrasion. Another desirable feature is that such compositions evidence color fastness evidence with minimal change of color in the purple or blue direction due to the effect of acid perspiration. It is especially desirable that such compositions with such improved color fastness characteristics be available for dyeing or coloring hair purple or blue, or to contribute chromophores in the purple or blue spectrum to hair dye product compositions.

SUMMARY OF THE INVENTION

The present invention is directed to hair dyeing compositions comprising:
(a) at least one coupler selected from the group consisting of compounds according to the following formula (1), formula (1-B), and formula (1-C):

formula (1)

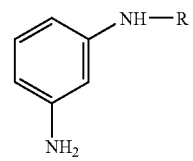

(1)

wherein R is a moiety selected from the following formulae (2), (3) or (4):

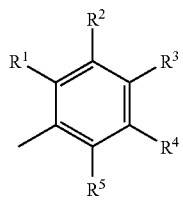

(2)

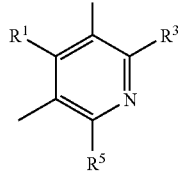

(3)

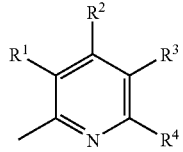

(4)

wherein $R^1$, $R^2$, $R^3$, $R^4$ and $R^5$ are each independently selected from the group consisting of hydrogen, halo, hydroxyl, amino, $C_1$-$C_4$ alkyl or haloalkyl, $C_1$-$C_4$ alkoxy or haloalkoxy, and nitrile;

formula (1-B)

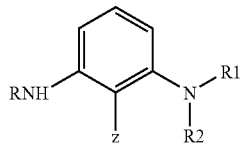

(1-B)

wherein $R^1$ is an aryl ring selected from the group consisting of phenyl and a 5- or 6-membered heteroaryl having one or more heteroatom selected from O, S, or N, wherein the aryl ring is unsubstituted or substituted with one or more substituents selected from the group consisting of hydrogen, halo, hydroxyl, amino, $C_1$-$C_4$ alkyl or haloalkyl, $C_1$-$C_4$ alkoxy or haloalkoxy, and nitrile;

wherein R and $R^2$ are each independently selected from the group consisting of hydrogen, $C_1$-$C_5$ alkyl, $C_1$-$C_5$ monohydroxyalkyl, and $C_2$-$C_5$ dihydroxyalkyl; and wherein Z is selected from the group consisting of $C_1$-$C_5$ alkyl, $C_1$-$C_5$ monohydroxyalkyl, $C_2$-$C_5$ dihydroxyalkyl, $C_1$-$C_5$ aminoalkyl, and $C_1$-$C_5$ methoxyalkyl; and formula (1-C)

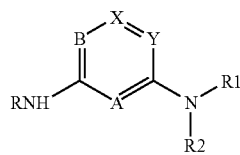

(1-C)

wherein $R^1$ is an aryl ring selected from the group consisting of phenyl and a 5- or 6-membered heteroaryl having one or more heteroatom selected from O, S, or N, wherein the aryl ring is unsubstituted or substituted with one or more substituents selected from the group consisting of hydrogen, halo, hydroxyl, amino, $C_1$-$C_4$ alkyl or haloalkyl, $C_1$-$C_4$ alkoxy or haloalkoxy, and nitrile;

wherein R and $R^2$ are each independently selected from the group consisting of hydrogen, $C_1$-$C_5$ alkyl, $C_1$-$C_5$ monohydroxyalkyl, and $C_2$-$C_5$ dihydroxyalkyl; and wherein any one of A, B, X, and Y is nitrogen and the remaining of A, B, X, and Y are each carbon;

(b) at least one primary intermediate of the formula (5):

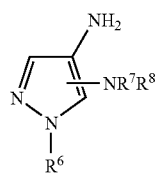

(5)

wherein $R^6$ and $R^7$ are independently selected from the group consisting of hydrogen, $C_1$-$C_4$ alkyl, $C_2$-$C_4$ hydroxyalkyl, benzyl, and phenyl; and wherein $R^8$ is selected from the group consisting of hydrogen, $C_1$-$C_4$ alkyl, and $C_2$-$C_4$ hydroxyalkyl;

or physiologically tolerated, water-soluble salts thereof; and (c) a suitable carrier.

These novel hair dyeing compositions are used to provide coloration to hair in which there is good dye uptake by the hair and provides shades or colors which are stable over a relatively long period of time. The novel compositions provide for dyeing of hair to impart color or shades, especially purple or blue, possessing good wash fastness, good selectivity, and do not undergo significant change on exposure to light, shampooing or acid perspiration. The hair dyeing compositions of the present invention are useful to provide purple or blue chromophores to hair dye product composition, whereby the shade imparted to the hair dye with such product compositions may be adjusted.

DETAILED DESCRIPTION OF THE INVENTION

While the specification concludes with claims that particularly point out and distinctly claim the invention, it is believed the present invention will be better understood from the following description.

As used herein, the term "hair dyeing composition" (also synonymously referred to herein as the hair dye composition, the hair coloring composition, or the hair dye lotion) refers to the composition containing oxidation dyes, including the compounds described herein, prior to admixture with the developer composition.

The term "developer composition" (also referred to as the oxidizing agent composition or the peroxide composition) refers to compositions containing an oxidizing agent prior to admixture with the hair dyeing composition.

The term "hair dye product" or "hair dye system" (also referred to as the hair dyeing system, hair dyeing product, or hair coloring system) interchangeably refer to the combination of the hair dyeing composition and the developer composition before admixture, and may further include a conditioner product and instructions, such product or system often being provided packaged as a kit.

The term "hair dyeing product composition" refers to the composition formed by mixing the hair dyeing composition and the developer composition.

The term "carrier" (or vehicle or base) refers to the combination of ingredients contained in a composition excluding the active agents (e.g., the oxidation hair dyes of the hair dyeing composition).

Unless otherwise indicated all percentages are by weight unless other unit basis are indicated.

Hair Dyeing Compositions

The hair dyeing compositions of the present invention comprise (a) at least one coupler selected from N-aryl-m-phenylenediamine derivatives of the formula (1), 2-substituted N-aryl-m-phenylenediamine derivatives of the formula (1-B), and N-aryl-m-diaminopyridine derivatives of the formula (1-C), in combination with at least one diaminopyrazole primary intermediate of the formula (5).

A. Couplers

1. N-Aryl-m-Phenylenediamine Derivatives of Formula (1)

In one embodiment of the present invention, the hair dyeing composition comprises at least one coupler selected from N-aryl-m-phenylenediamine derivatives according to the formula (1):

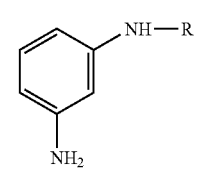

(1)

wherein R is a moiety selected from the following formulae (2), (3) or (4):

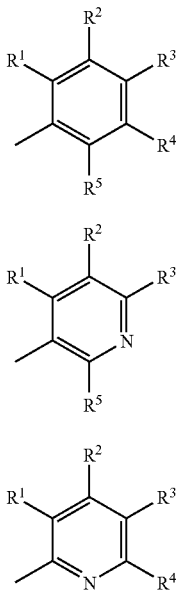

wherein $R^1$, $R^2$, $R^3$, $R^4$ and $R^5$ are each independently selected from the group consisting of hydrogen, halo, hydroxyl, amino, $C_1$-$C_4$ alkyl or haloalkyl, $C_1$-$C_4$ alkoxy or haloalkoxy, and nitrile.

For example, the N-aryl-m-phenylenediamine derivatives according to the formula (1) are coupler compounds selected from the group consisting of N-phenyl-benzene-1,3-diamine, N-(4-amino-phenyl)-benzene-1,3-diamine, 4-methoxyphenyl-(3-amino-phenyl)-amine, and 3-methoxyphenyl-(3-amino-phenyl)-amine.

The coupler compounds of formula (1) may be prepared according to the following reaction sequence where R is as defined hereinbefore.

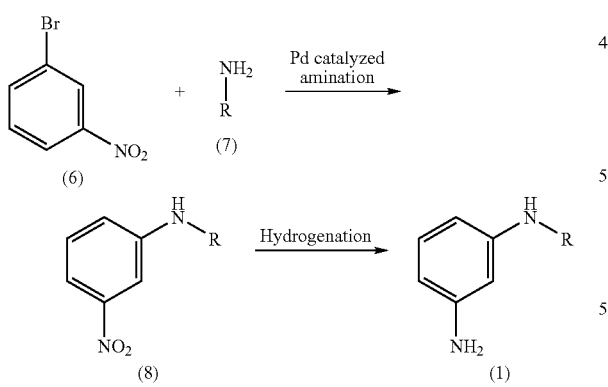

In this reaction, 1-bromo-3-nitrobenzene (6) is subjected to palladium catalyzed amination with an aryl amine of the formula R—$NH_2$ (7) to produce an N-aryl-m-nitro-aminobenzene (8) that, when subjected to hydrogenation, produces an N-aryl-m-benzenediamine (1).

Using the above-described synthesis procedure, the following two example coupler compounds were prepared.

SYNTHESIS EXAMPLE 1

Synthesis of 4-methoxyphenyl-(3-amino-phenyl)-amine

A suspension of 1-bromo-3-nitrobenzene (6) (2 mmol, 0.40 g), p-methoxyaniline (7) (2.4 mmol, 0.30 g), sodium-tert-butoxide (2.8 mmol, 0.26 g), $Pd_2(dba)_3$ (10% mol, 0.18 g), BINAP (10% mol, 0.13 g) in toluene (4 mL, 0.5 M) was stirred for 18 h at 100° $C^1$. The mixture was cooled to room temperature, filtered on celite and washed with ethyl acetate (3×5 mL). The combined organic layer was washed with water (3×5 mL), dried with $Na_2SO_4$, evaporated, and purified (silica, 100% hexane) to give yellow-brownish powder (8) (0.1 g, 23% yield): $^1$H NMR (DMSO-$d_6$) δ 8.46 (s, 1H), 7.61 (t, 1H), 7.49 (d, 1H), 7.40 (t, 1H), 7.25 (d, 1H), 7.15 (d, 2H), 6.95 (d, 2H), 3.80 (s, 3H). Hydrogenation of (8) (0.1 g) with Pd/C (10%, 0.01 g) in MeOH (20 mL) for 2 h at 60 psi $H_2$ gave 4-methoxyphenyl-(3-amino-phenyl)-amine (1) (0.04 g, 45% yield): $^1$H NMR (DMSO-$d_6$) δ 7.51 (s, 1H), 7.00 (d, 2H), 6.82 (d, 3H), 6.20 (s, 1H), 6.12 (s, 1H), 5.99 (d, 1H), 4.48 (s, 2H), 3.75 (s, 3H); MS 214 ($M^+$), 199, 182, 169, 154, 107, 91, 85, 65.

1: R. A. Singer, J. P. Dadighi and S. L. Buchwald, J. Am. Chem. Soc. 1998, 120, 213.

SYNTHESIS EXAMPLE 2

Synthesis of 3-methoxyphenyl-(3-amino-phenyl)-amine

The compound 3-methoxyphenyl-(3-amino-phenyl)-amine was prepared according to the procedure described above of Synthesis Example 1 by substituting m-methoxyaniline for p-methoxyaniline as reactant (7). The product is characterized by the following parameters: $^1$H NMR (DMSO-$d_6$) δ 7.93 (s, 1H), 7.16 (d, 1H), 6.90 (t, 1H), 6.63 (d, 2H), 6.43 (t, 2H), 6.30 (d, 1H), 6.13 (d, 1H), 5.23 (s, 2H), 3.70 (s, 3H); MS 214 ($M^+$), 213, 198, 182, 169, 154, 143, 127, 107, 91, 85, 65.

2. 2-Substituted N-Aryl-m-Phenylenediamine Derivatives of Formula (1-B)

In another embodiment of the present invention, the hair dyeing composition comprises at least one coupler selected from 2-substituted N-aryl-m-phenylenediamine derivatives according to the formula (1-B):

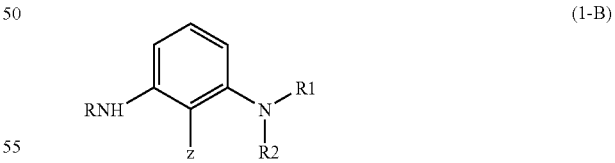

wherein $R^1$ is an aryl ring selected from the group consisting of phenyl and a 5- or 6-membered heteroaryl having one or more heteroatom selected from O, S, or N, and wherein the aryl ring is unsubstituted or substituted with one or more substituents selected from the group consisting of hydrogen, halo, hydroxyl, amino, $C_1$-$C_4$ alkyl or haloalkyl, $C_1$-$C_4$ alkoxy or haloalkoxy, and nitrile;

wherein R and $R^2$ are each independently selected from the group consisting of hydrogen, $C_1$-$C_5$ alkyl, $C_1$-$C_5$ monohydroxyalkyl, and $C_2$-$C_5$ dihydroxyalkyl; and wherein Z is selected from the group consisting of $C_1$-$C_5$ alkyl, $C_1$-$C_5$ monohydroxyalkyl, $C_2$-$C_5$ dihydroxyalkyl, $C_1$-$C_5$ aminoalkyl, and $C_1$-$C_5$ methoxyalkyl.

For example, the 2-substituted N-aryl-m-phenylenediamine derivatives according to the formula (1-B) are coupler compounds selected from the group consisting of N2-(3-amino-2-methyl-phenyl)-pyridine-2,5-diamine, N-(4-amino-phenyl)-2-methyl-benzene-1,3-diamine, N-(4-amino-phenyl)-N'-ethyl-2-methyl-benzene-1,3-diamine, 2-[2-amino-6-(4-amino-phenylamino)-phenyl]-ethanol, 2-[[4-(3-amino-2-methyl-phenylamino)-phenyl]-(2-hydroxy-ethyl)-amino]-ethanol, 2-methyl-N-(4-pyrrolidin-1-yl-phenyl)-benzene-1,3-diamine, 2-Aminomethyl-N-(4-amino-phenyl)-benzene-1,3-diamine, [2-amino-6-(4-aminophenylamino)-phenyl]-methanol, N-(4-amino-phenyl)-2-methoxymethyl-benzene-1,3-diamine, N1-[3-amino-2-(aminomethyl)phenyl]benzene-1,4-diamine, N1-[3-amino-2-(cyanomethyl)phenyl]benzene-1,4-diamine, N1-(3-amino-2-vinylphenyl)benzene-1,4-diamine, N1-[3-amino-2-(hydroxymethyl)phenyl]benzene-1,4-diamine, 2-[N-(3-aminophenyl)-N-(4-aminophenyl)amino]ethanol, N1-[3-amino-2-(1-hydroxyethyl)phenyl]benzene-1,4-diamine, N1,N1-bis(2-hydroxyethyl)-N-4-(3'-aminophenyl)-1,4-diaminobenzene, N1-{3-amino-2-[(E)-prop-1-enyl]phenyl}benzene-1,4-diamine, 1-(4-aminophenyl)-1,2,3,4-tetrahydroquinolin-5-amine, 1-(4-aminophenyl)indolin-4-amine, N1-(1,2-dihydroquinolin-5-yl)benzene-1,4-diamine, and N1-(indolin-4-yl)benzene-1,4-diamine.

The coupler compounds of formula (1-B) and may be prepared according to the reaction sequences described below.

3. N-Aryl-m-Diaminopyridine Derivatives of Formula (1-C)

In a further embodiment of the present invention, the hair dyeing composition comprises at least one coupler selected from N-aryl-m-diaminopyridine derivatives of the formula (1-C):

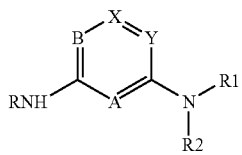

(1-C)

wherein $R^1$ is an aryl ring selected from the group consisting of phenyl and a 5- or 6-membered heteroaryl having one or more heteroatom selected from O, S, or N, and wherein the aryl ring is unsubstituted or substituted with one or more substituents selected from the group consisting of hydrogen, halo, hydroxyl, amino, $C_1$-$C_4$ alkyl or haloalkyl, $C_1$-$C_4$ alkoxy or haloalkoxy, and nitrile;

wherein R and $R^2$ are each independently selected from the group consisting of hydrogen, $C_1$-$C_5$ alkyl, $C_1$-$C_5$ monohydroxyalkyl, and $C_2$-$C_5$ dihydroxyalkyl; and wherein any one of A, B, X, and Y is nitrogen and the remaining of A, B, X, and Y are each carbon.

For example, the N-aryl-m-diaminopyridine derivatives according to the formula (1-C) are coupler compounds selected from the group consisting of N-(4-amino-phenyl)-pyridine-2,6-diamine, N-(5-amino-pyridin-2-yl)pyridine-2,6-diamine, N-(5-aminopyridin-2-yl)benzene-1,3-diamine, N-(4-pyrrolidin-1-yl-phenyl)-pyridine-2,6-diamine, N-(4-amino-phenyl)-N'-methyl-pyridine-2,6-diamine, 2-[4-(6-methylamino-pyridin-2-ylamino)-phenylamino]-ethanol, 2-[6-(4-amino-phenylamino)-pyridin-2-ylamino]-ethanol, N-(4-amino-phenyl)-N-methyl-pyridine-2,6-diamine, N-(1H-pyrrol-2-yl)-pyridine-2,6-diamine, N-(6-amino-pyridin-2-yl)-pyrimidine-2,4,5,6-tetraamine, N-(5-amino-[1,3,4]thiadiazol-2-yl)-pyridine-2,6-diamine, N3-(4-aminophenyl)pyridine-3,5-diamine, N3-(4-aminophenyl)-N-5-(2-hydroxyethyl)pyridine-3,5-diamine, N3-(thiazol-2-yl)pyridine-3,5-diamine, N2-(4-aminophenyl)pyridine-2,4-diamine, N2-(4-aminophenyl)-5-chloropyridine-2,6-diamine, N2-(4-aminophenyl)-5-methoxypyridine-2,6-diamine, N3-(4-aminophenyl)-N-3-methylpyridine-3,5-diamine, N3-(5-aminopyridin-2-yl)pyridine-3,5-diamine, N3-(4,5,6-triaminopyrimidin-2-yl)pyridine-3,5-diamine, N2-(4-aminophenyl)-N2-methylpyridine-2,4-diamine, N4-(4-aminophenyl)-N-4-methylpyridine-2,4-diamine, N2-(4-aminophenyl)-3-chloropyridine-2,6-diamine, and N2-(4-aminophenyl)-3-methoxypyridine-2,6-diamine.

The coupler compounds of formula (1-B) and formula (1-C) may be prepared according to the following reaction sequence:

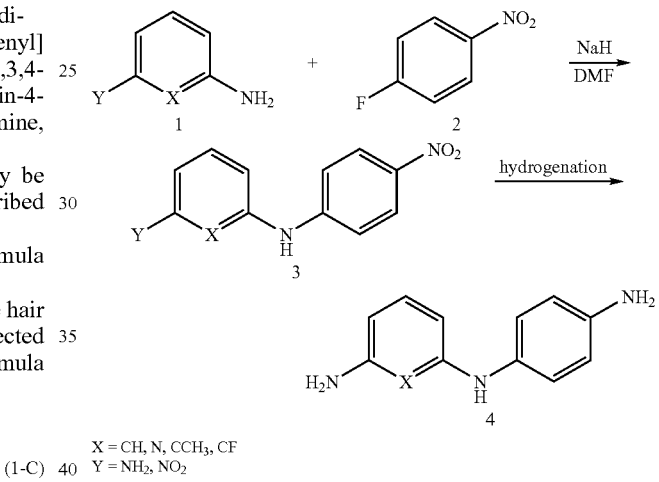

X = CH, N, CCH₃, CF
Y = NH₂, NO₂

In this reaction sequence, reaction of compound 1 with 1-fluoro-4-nitrobenzene 2 in the presence of sodium hydride in DMF affords compound 3. Hydrogenation of compound 3 with hydrogen and Pd/C in methanol produces compound 4.

wherein R and $R^2$ are each independently selected from the group consisting of hydrogen, $C_1$-$C_5$ alkyl, $C_1$-$C_5$ monohydroxyalkyl, and $C_2$-$C_5$ dihydroxyalkyl; and wherein any one of A, B, X, and Y is nitrogen and the remaining of A, B, X, and Y are each carbon.

For example, the N-aryl-m-diaminopyridine derivatives according to the formula (1-C) are coupler compounds selected from the group consisting of N-(4-amino-phenyl)-pyridine-2,6-diamine, N-(5-amino-pyridin-2-yl)pyridine-2,6-diamine, N-(5-aminopyridin-2-yl)benzene-1,3-diamine, N-(4-pyrrolidin-1-yl-phenyl)-pyridine-2,6-diamine, N-(4-amino-phenyl)-N'-methyl-pyridine-2,6-diamine, 2-[4-(6-methylamino-pyridin-2-ylamino)-phenylamino]-ethanol, 2-[6-(4-amino-phenylamino)-pyridin-2-ylamino]-ethanol, N-(4-amino-phenyl)-N-methyl-pyridine-2,6-diamine, N-(1H-pyrrol-2-yl)-pyridine-2,6-diamine, N-(6-amino-pyridin-2-yl)-pyrimidine-2,4,5,6-tetraamine, N-(5-amino-[1,3,4]thiadiazol-2-yl)-pyridine-2,6-diamine, N3-(4-aminophenyl)pyridine-3,5-diamine, N3-(4-aminophenyl)-N-5-(2-hydroxyethyl)pyridine-3,5-diamine, N3-(thiazol-2-yl)

pyridine-3,5-diamine, N2-(4-aminophenyl)pyridine-2,4-diamine, N2-(4-aminophenyl)-5-chloropyridine-2,6-diamine, N2-(4-aminophenyl)-5-methoxypyridine-2,6-diamine, N3-(4-aminophenyl)-N-3-methylpyridine-3,5-diamine, N3-(5-aminopyridin-2-yl)pyridine-3,5-diamine, N3-(4,5,6-triaminopyrimidin-2-yl)pyridine-3,5-diamine, N2-(4-aminophenyl)-N2-methylpyridine-2,4-diamine, N4-(4-aminophenyl)-N-4-methylpyridine-2,4-diamine, N2-(4-aminophenyl)-3-chloropyridine-2,6-diamine, and N2-(4-aminophenyl)-3-methoxypyridine-2,6-diamine.

The coupler compounds of formula (1-B) and formula (1-C) may be prepared according to the following reaction sequence:

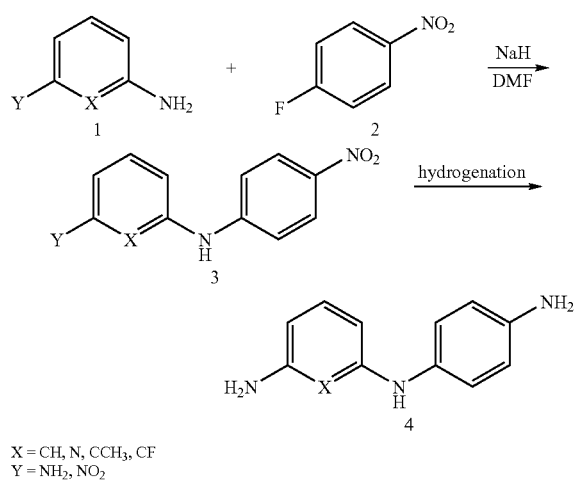

X = CH, N, CCH₃, CF
Y = NH₂, NO₂

In this reaction sequence, reaction of compound 1 with 1-fluoro-4-nitrobenzene 2 in the presence of sodium hydride in DMF affords compound 3. Hydrogenation of compound 3 with hydrogen and Pd/C in methanol produces compound 4.

Using the above-described synthesis procedure, the following example coupler compound was prepared.

SYNTHESIS EXAMPLE 3

Synthesis of N-(4-amino-phenyl)-pyridine-2,6-diamine 2,6-Diaminopyridine (9.2 mmol, 1.0 g) and 1-fluoro-4-nitrobenzene (9.2 mmol, 1.3 g) were dissolved in 10 mL anhydrous DMF. The solution was stirred at ambient temperature while 95% sodium hydride (18.3 mmol, 440 mg) was added. The solution turned reddish black in 30 min. The reaction mixture was stirred for an additional 20 hours at room temperature. The reaction mixture was poured slowly into 25 mL 10% aqueous NH₄Cl solution mixed with ice (25 g). The resulted aqueous solution was extracted with EtOAc (4×30 mL). The combined organic phase was dried over MgSO₄ and evaporated to dryness. The residual oil was purified by flash column chromatography on silica gel (EtOAc:Hexane 1:2) to provide N2-(4-nitrophenyl)pyridine-2,6-diamine (1.6 g, 76%), a reddish orange crystal: ¹H NMR (500 MHz, CDCl₃) δ 8.19 (d, 2H, J=9.0 Hz), 7.51 (d, 2H, J=9.0 Hz), 7.42 (t, 1H, J=8.0 Hz), 6.85 (s, 1H), 6.30 (d, 1H, J=8.0 Hz), 6.16 (d, 1H, J=8.0 Hz), 4.51 (s, 2H); MS m/z (relative intensity) 231 (M+1, 100), 184 (100). N2-(4-nitrophenyl)pyridine-2,6-diamine (2.6 mmol, 0.6 g) and 10% Pd/C (30 mg) were added to a 20 mL test tube equipped with a stir bar and then dry ice (0.5 g, CO₂) was added to the mixture just before MeOH (8 mL) was added. The suspension was then put into a pressure vessel under 80 psi H₂. The reaction mixture was stirred for 3 hours. The solution turned from yellow to colorless. The reaction mixture was transferred into a 10 mL syringe and filtered through an Acrodisc syringe Filter into a 100 mL round bottom flask containing 37% aqueous HCl (4 mL). The solvent was then evaporated and azeotroped to dryness with toluene and absolute ethanol (3×30 mL of 1:1 mixture). The product was obtained as an off-white powder in quantitative yield: ¹H NMR (500 MHz, D₂O) δ 7.48 (t, 1H, J=14.0 Hz), 7.25 (m, 4H), 6.13 (d, 1H, J=14.0 Hz), 6.09 (d, 1H, J=14.0 Hz); Ms m/z (relative intensity) 201 (M+1, 100).

The coupler compounds of formula (1-B) and formula (1-C) also may be prepared according to the following reaction sequence:

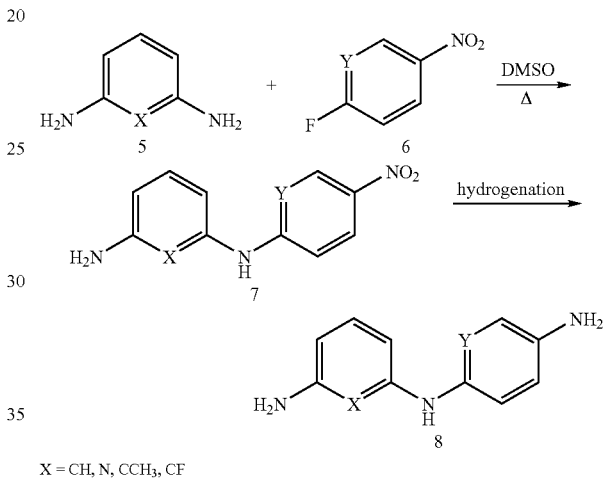

X = CH, N, CCH₃, CF
Y = CH, N, CF

In this reaction sequence, the aromatic substitution of compound 6 with compound 5 in hot DMSO gives rise to compound 7. Hydrogenation of compound 7 with hydrogen and Pd/C in MeOH produces compound 8.

Using the above-described synthesis procedure, the following two example coupler compounds were prepared.

SYNTHESIS EXAMPLE 4

Synthesis of N-(5-amino-pyridin-2-yl)pyridine-2,6-diamine 2,6-Diaminopyridine (9.2 mmol, 1.0 g) and 2-fluoro-5-nitropyridine (4.6 mmol, 0.65 g) were dissolved in 6 mL of DMSO. The solution was heated to 80° C. for 18 h. The solution eventually turned dark red. The reaction mixture was cooled to room temperature and purified directly by flash column chromatography (silica, EtOAc:Hexanes=1:3) to give N²-(5-nitropyridin-2-yl)pyridine-2,6-diamine as a reddish crystalline solid (0.21 g, 20% yield): ¹H NMR (500 MHz, CDCl₃) δ 9.13 (d, 1H, J=3.0 Hz), 8.36 (dd, 1H, J=3.0 Hz, J₂=9.5 Hz), 7.94 (d, 1H, J=9.5 Hz), 7.66 (s, 1H), 7.46 (t, 1H, J=8.0 Hz), 6.68 (d, 1H, J=8.0 Hz), 6.23 (d, 1H, J=8.0 Hz), 4.46 (s, 2H); Ms m/z (relative intensity) 232 (M+1, 100), 186 (57). The nitro compound (0.78 mmol, 0.18 g) and 10% Pd/C (20 mg) were added to a 20 mL test tube equipped with a stir bar, dry ice (0.5 g) was added to the mixture just before MeOH (7 mL) was added. The suspension was then put into a pressure vessel under 80 psi of $H_2$. The reaction mixture was stirred for 2 hours. The solution turned from yellow to colorless. The reaction mixture was transferred into a 10 mL syringe and was then filtered through an Acrodisc syringe Filter into a 100 mL round bottom flask containing 37% aqueous HCl (4 mL). The solvent was then evaporated and azeotroped to dryness with toluene and absolute ethanol (3×30 mL of 1:1 mixture). The product was obtained as a grayish yellow powder in quantitative yield.

SYNTHESIS EXAMPLE 5

Synthesis of N-(5-aminopyridin-2-yl)benzene-1,3-diamine m-Phenylenediamine (2.8 mmol, 0.30 g) and 2-fluoro-5-nitropyridine (0.92 mmol, 0.13 g) were dissolved in 6 mL of DMSO. The solution was heated to 80° C. for 18 hours. The solution eventually turned dark red. The reaction mixture was cooled to room temperature and purified directly by flash column chromatography (silica, EtOAc:Hexanes=1:3) to give $N^1$-(5-nitropyridin-2-yl)benzene-1,3-diamine as a reddish crystalline compound (0.19 g, 89% yield): $^1$H NMR (500 MHz, CDCl$_3$) δ 9.08 (d, 1H, J=2.5 Hz), 8.24 (dd, 1H, $J_1$=2.5 Hz, $J_2$=9.5 Hz), 7.281 (s, 1H), 7.19 (t, 1H, J=8.0 Hz), 6.82 (d, 1H, J=9.5 Hz), 6.74 (s, 1H), 6.70 (d, 1H, J=8.0 Hz), 6.56 (d, 1H, J=7.5 Hz), 3.80 (br, 2H); $^{13}$C NMR (125 MHz, CDCl$_3$) δ 159.91, 148.05, 146.93, 139.09, 137.15, 133.59, 130.77, 112.80, 112.66, 109.13, 106.67. The nitro compound (0.43 mmol, 0.10 g) and 10% Pd/C (10 mg) were added to a 20 mL test tube equipped with a stir bar, dry ice (0.5 g) was added to the mixture just before MeOH (7 mL) was added. The suspension was then put into a pressure vessel under 80 psi of $H_2$. The reaction mixture was stirred for 2 hours. The solution turned from yellow to colorless. The reaction mixture was transferred into a 10 mL syringe and filtered through an Acrodisc syringe Filter into a 100 mL round bottom flask containing 37% aqueous HCl (3 mL). The solvent was then evaporated and azeotroped to dryness with toluene and absolute ethanol (3×30 mL of 1:1 mixture). The product was obtained as a grayish yellow powder in quantitative yield.

B. Primary Intermediates of Formula (5)

The hair dyeing compositions of the present invention, in combination with the above described couplers, also comprise at least one diaminopyrazole primary intermediate of the formula (5):

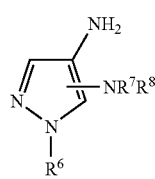

(5)

wherein $R^6$ and $R^7$ are independently selected from the group consisting of hydrogen, $C_1$-$C_4$ alkyl, $C_2$-$C_4$ hydroxyalkyl, benzyl, and phenyl; and wherein $R^8$ is selected from the group consisting of hydrogen, $C_1$-$C_4$ alkyl, and $C_2$-$C_4$ hydroxyalkyl;

or physiologically tolerated, water-soluble salts thereof.

For example, the diaminopyrazole primary intermediate is the compound 2-(4,5-diamino-pyrazol-1-yl)-ethanol, i.e., a compound of Formula 5 wherein $R^6$ is a hydroxyethyl group, $R^7$ and $R^8$ are each hydrogen atoms, and the $NR^7R^8$ moiety is at the 5-position.

The diaminopyrazole primary intermediates of formula (5) may be prepared by the processes described in U.S. Pat. No. 5,061,289.

C. Auxiliary Primary Intermediates and Auxiliary Couplers

For hair coloring compositions of this invention, there may be used one or more of the N-aryl-m-phenylenediamine derivatives, the 2-substituted N-aryl-m-phenylenediamine derivatives, and/or the N-aryl-m-diaminopyridine derivatives as couplers in combination with one or more diaminopyrazole primary intermediates. The hair coloring compositions of this invention may also include one or more auxiliary primary intermediate compounds and/or one or more auxiliary coupler compounds, if so desired.

Suitable known primary intermediates include, for example:

p-phenylenediamine derivatives such as: benzene-1,4-diamine (commonly known as p-phenylenediamine), 2-methyl-benzene-1,4-diamine, 2-chloro-benzene-1,4-diamine, N-phenyl-benzene-1,4-diamine, N-(2-ethoxyethyl)benzene-1,4-di amine, 2-[(4-amino-phenyl)-(2-hydroxy-ethyl)-amino]-ethanol, (commonly known as N,N-bis(2-hydroxyethyl)-p-phenylenediamine) (2,5-diamino-phenyl)-methanol, 1-(2,5-diamino-phenyl)-ethanol, 2-(2,5-diaminophenyl)-ethanol, N-(4-aminophenyl)benzene-1,4-diamine, 2,6-dimethyl-benzene-1,4-diamine, 2-isopropyl-benzene-1,4-diamine, 1-[(4-aminophenyl)amino]-propan-2-ol, 2-propyl-benzene-1,4-diamine, 1,3-bis[(4-aminophenyl)(2-hydroxyethyl)amino]propan-2-ol, $N^4,N^4$,2-trimethylbenzene-1,4-diamine, 2-methoxy-benzene-1,4-diamine, 1-(2,5-diaminophenyl)ethane-1,2-diol, 2,3-dimethyl-benzene-1,4-diamine, N-(4-amino-3-hydroxy-phenyl)-acetamide, 2,6-diethylbenzene-1,4-diamine, 2,5-dimethylbenzene-1,4-diamine, 2-thien-2-ylbenzene-1,4-diamine, 2-thien-3-ylbenzene-1,4-diamine, 2-pyridin-3-ylbenzene-1,4-diamine, 1,1'-biphenyl-2,5-di amine, 2-(methoxymethyl)benzene-1,4-diamine, 2-(aminomethyl)benzene-1,4-diamine, 2-(2,5-diaminophenoxy)ethanol, N-[2-(2,5-diaminophenoxy)ethyl]-acetamide, N,N-dimethylbenzene-1,4-diamine, N,N-diethylbenzene-1,4-diamine, N,N-dipropylbenzene-1,4-diamine, 2-[(4-aminophenyl)(ethyl)amino]ethanol, 2-[(4-amino-3-methyl-phenyl)-(2-hydroxy-ethyl)-amino]-ethanol, N-(2-methoxyethyl)-benzene-1,4-diamine, 3-[(4-aminophenyl)amino]propan-1-ol, 3-[(4-aminophenyl)-amino]propane-1,2-diol, N-{4-[(4-aminophenyl)amino]butyl}benzene-1,4-diamine, and 2-[2-(2-{2-[(2,5-diaminophenyl)-oxy]ethoxy}ethoxy)ethoxy]benzene-1,4-diamine;

p-aminophenol derivatives, such as: 4-amino-phenol (commonly known as p-aminophenol), 4-methylamino-phenol, 4-amino-3-methyl-phenol, 4-amino-2-hydroxymethyl-phenol, 4-amino-2-methyl-phenol, 4-amino-2-[(2-hydroxyethylamino)-methyl]-phenol, 4-amino-2-methoxymethyl-phenol, 5-amino-2-hydroxy-benzoic acid, 1-(5-amino-2-hydroxy-phenyl)-ethane-1,2-diol, 4-amino-2-(2-hydroxyethyl)-phenol, 4-amino-3-(hydroxymethyl)phenol, 4-amino-3-fluoro-phenol, 4-amino-2-(aminomethyl)-phenol, and 4-amino-2-fluoro-phenol;

o-aminophenol derivatives, such as: 2-amino-phenol (commonly known as o-aminophenol), 2,4-diaminophenol, 2-amino-5-methyl-phenol, 2-amino-6-methyl-phenol, N-(4-amino-3-hydroxy-phenyl)-acetamide, and 2-amino-4-methyl-phenol; and heterocyclic derivatives, such as: pyrimidine-2,4,5,6-tetramine (commonly known as 2,4,5,6-tetraminopyridine), 1-methyl-1H-pyrazole-4,5-diamine, 2-(4,5-diamino-1H-pyrazol-1-yl)ethanol, $N^2,N^2$-dimethyl-pyridine-2,5-diamine, 2-[(3-amino-6-methoxypyridin-2-yl)amino]ethanol, 6-methoxy-$N^2$-methyl-pyridine-2,3-diamine, 2,5,6-triaminopyrimidin-4(1H)-one, pyridine-2,5-diamine, 1-isopropyl-1H-pyrazole-4,5-diamine, 1-(4-methylbenzyl)-1H-pyrazole-4,5-diamine, 1-(benzyl)-1H-pyrazole-4,5-diamine, and 1-(4-chlorobenzyl)-1H-pyrazole-4,5-diamine.

Suitable known couplers include, for example:

phenols, resorcinol and naphthol derivatives, such as: naphthalene-1,7-diol, benzene-1,3-diol, 4-chlorobenzene-1,3-diol, naphthalen-1-ol, 2-methyl-naphthalen-1-ol, naphthalene-1,5-diol, naphthalene-2,7-diol, benzene-1,4-diol, 2-methyl-benzene-1,3-diol, 7-amino-4-hydroxy-naphthalene-2-sulfonic acid, 2-isopropyl-5-methylphenol, 1,2,3,4-tetrahydro-naphthalene-1,5-diol, 2-chloro-benzene-1,3-diol, 4-hydroxy-naphthalene-1-sulfonic acid, benzene-1,2,3-triol, naphthalene-2,3-diol, 5-dichloro-2-methylbenzene-1,3-diol, 4,6-dichlorobenzene-1,3-diol, and 2,3-dihydroxy-[1,4]naphthoquinone;

m-phenylenediamines, such as: 2,4-diaminophenol, benzene-1,3-diamine, 2-(2,4-diamino-phenoxy)-ethanol, 2-[(3-amino-phenyl)-(2-hydroxy-ethyl)-amino]-ethanol, 2-methyl-benzene-1,3-diamine, 2-[[2-(2,4-diamino-phenoxy)-ethyl]-(2-hydroxy-ethyl)-amino]-ethanol, 4-{3-[(2,4-diaminophenyl)oxy]propoxy}benzene-1,3-diamine, 2-(2,4-diamino-phenyl)-ethanol,2-(3-amino-4-methoxy-phenylamino)-ethanol, 4-(2-amino-ethoxy)-benzene-1,3-diamine, (2,4-diamino-phenoxy)-acetic acid, 2-[2,4-diamino-5-(2-hydroxy-ethoxy)-phenoxy]-ethanol, 4-ethoxy-6-methyl-benzene-1,3-diamine, 2-(2,4-diamino-5-methyl-phenoxy)-ethanol, 4,6-dimethoxy-benzene-1,3-diamine, 2-[3-(2-hydroxy-ethylamino)-2-methyl-phenylamino]-ethanol, 3-(2,4-diamino-phenoxy)-propan-1-ol, N-[3-(dimethylamino)phenyl]urea, 4-methoxy-6-methyl-benzene-1,3-diamine, 4-fluoro-6-methylbenzene-1,3-diamine, 2-({3-[(2-hydroxyethyl)amino]-4,6-dimethoxyphenyl}-amino)ethanol, 3-(2,4-diaminophenoxy)-propane-1,2-diol, 2-[2-amino-4-(methylamino)-phenoxy]ethanol, 2-[(5-amino-2-ethoxy-phenyl)-(2-hydroxy-ethyl)-amino]-ethanol, 2-[(3-aminophenyl)amino]ethanol, N-(2-aminoethyl)benzene-1,3-diamine, 4-{[(2,4-diamino-phenyl)oxy]methoxy}-benzene-1,3-diamine, and 2,4-dimethoxybenzene-1,3-diamine;

m-aminophenols, such as: 3-amino-phenol, 2-(3-hydroxy-4-methyl-phenylamino)-acetamide, 2-(3-hydroxy-phenylamino)-acetamide, 5-amino-2-methyl-phenol, 5-(2-hydroxy-ethylamino)-2-methyl-phenol, 5-amino-2,4-dichloro-phenol, 3-amino-2-methyl-phenol, 3-amino-2-chloro-6-methyl-phenol, 5-amino-2-(2-hydroxy-ethoxy)-phenol, 2-chloro-5-(2,2,2-trifluoro-ethylamino)-phenol, 5-amino-4-chloro-2-methyl-phenol, 3-cyclopentylamino-phenol, 5-[(2-hydroxyethyl)amino]-4-methoxy-2-methylphenol, 5-amino-4-methoxy-2-methylphenol, 3-(dimethylamino)phenol, 3-(diethylamino)phenol, 5-amino-4-fluoro-2-methylphenol, 5-amino-4-ethoxy-2-methylphenol, 3-amino-2,4-dichloro-phenol, 3-[(2-methoxyethyl)amino]phenol, 3-[(2-hydroxyethyl)amino]phenol, 5-amino-2-ethyl-phenol, 5-amino-2-methoxyphenol, 5-[(3-hydroxypropyl)amino]-2-methylphenol, 3-[(3-hydroxy-2-methylphenyl)-amino]propane-1,2-diol, and 3-[(2-hydroxyethyl)amino]-2-methylphenol; and heterocyclic derivatives, such as: 3,4-dihydro-2H-1,4-benzoxazin-6-ol, 4-methyl-2-phenyl-2,4-dihydro-3H-pyrazol-3-one, 6-methoxyquinolin-8-amine, 4-methylpyridine-2,6-diol, 2,3-dihydro-1,4-benzodioxin-5-ol, 1,3-benzodioxol-5-ol, 2-(1,3-benzodioxol-5-ylamino)ethanol, 3,4-dimethylpyridine-2,6-diol, 5-chloropyridine-2,3-diol, 2,6-dimethoxypyridine-3,5-diamine, 1,3-benzodioxol-5-amine, 2-{[3,5-diamino-6-(2-hydroxy-ethoxy)-pyridin-2-yl]oxy}-ethanol, 1H-indol-4-ol, 5-amino-2,6-dimethoxypyridin-3-ol, 1H-indole-5,6-diol, 1H-indol-7-ol, 1H-indol-5-ol, 1H-indol-6-ol, 6-bromo-1,3-benzodioxol-5-ol, 2-aminopyridin-3-ol, pyridine-2,6-diamine, 3-[(3,5-diaminopyridin-2-yl)oxy]propane-1,2-diol, 5-[(3,5-diaminopyridin-2-yl)oxy]pentane-1,3-diol, 1H-indole-2,3-dione, indoline-5,6-diol, 3,5-dimethoxypyridine-2,6-diamine, 6-methoxypyridine-2,3-diamine, and 3,4-dihydro-2H-1,4-benzoxazin-6-amine.

Understandably, the coupler compounds and the primary intermediate compounds, including the compounds according to formulas (1), (1-B), (1-C), and (5) of this invention, in so far as they are bases, can be used as free bases or in the form of their physiologically compatible salts with organic or inorganic acids, such as hydrochloric, citric, acetic, tartaric, or sulfuric acids, or, in so far as they have aromatic OH groups, in the form of their salts with bases, such as alkali phenolates.

The total amount of dye precursors (e.g., primary intermediate and coupler compounds, including the compounds of this invention) in the hair dyeing compositions of this invention is generally from about 0.002 to about 20, preferably from about 0.04 to about 10, and most preferably from about 0.1 to about 7.0 weight percent, based on the total weight of the hair dyeing composition. The primary intermediate and coupler compounds are generally used in molar equivalent amounts. However, it is possible to use the primary intermediate compounds in either excess or deficiency, i.e., a molar ratio of primary intermediate to coupler generally ranging from about 5:1 to about 1:5.

The hair dyeing compositions of this invention will contain the primary intermediate and coupler combination of this invention in an effective dyeing amount, each of the primary intermediate and coupler being generally in an amount of from about 0.001 to about 10 weight percent by weight of the hair dye composition, preferably from about 0.01 to about 5.0 weight percent. Other couplers, when present, are typically present in an amount such that in aggregate the concentration of couplers in the composition is from about 0.002 to about 10 weight percent, preferably from about 0.01 to about 5.0 weight percent. Other primary intermediates when present are present in an effective dyeing concentration, generally an amount of from about 0.001 to about 10.0 weight percent by weight of the hair dye composition, preferably from about 0.01 to about 5.0 weight percent. The remainder of dimethoxypyridine-3,5-diamine, 1,3-benzodioxol-5-amine, 2-{[3,5-diamino-6-(2-hydroxy-ethoxy)-pyridin-2-yl]oxy}-ethanol, 1H-indol-4-ol, 5-amino-2,6-dimethoxypyridin-3-ol, 1H-indole-5,6-diol, 1H-indol-7-ol, 1H-indol-5-ol, 1H-indol-6-ol, 6-bromo-1,3-benzodioxol-5-ol, 2-aminopyridin-3-ol, pyridine-2,6-diamine, 3-[(3,5-diaminopyridin-2-yl)oxy]propane-1,2-diol, 5-[(3,5-diaminopyridin-2-yl)oxy]pentane-1,3-diol, 1H-indole-2,3-dione, indoline-5,6-diol, 3,5-dimethoxypyridine-2,6-diamine, 6-methoxypyridine-2,3-diamine, and 3,4-dihydro-2H-1,4-benzoxazin-6-amine.

Understandably, the coupler compounds and the primary intermediate compounds, including the compounds according to formulas (1), (1-B), (1-C), and (5) of this invention, in so far as they are bases, can be used as free bases or in the form of their physiologically compatible salts with organic or inorganic acids, such as hydrochloric, citric, acetic, tartaric, or sulfuric acids, or, in so far as they have aromatic OH groups, in the form of their salts with bases, such as alkali phenolates.

The total amount of dye precursors (e.g., primary intermediate and coupler compounds, including the compounds of this invention) in the hair dyeing compositions of this invention is generally from about 0.002 to about 20, preferably from about 0.04 to about 10, and most preferably from about 0.1 to about 7.0 weight percent, based on the total weight of the hair dyeing composition. The primary intermediate and coupler compounds are generally used in molar equivalent amounts. However, it is possible to use the primary intermediate compounds in either excess or deficiency, i.e., a molar ratio of primary intermediate to coupler generally ranging from about 5:1 to about 1:5.

The hair dyeing compositions of this invention will contain the primary intermediate and coupler combination of this invention in an effective dyeing amount, each of the primary intermediate and coupler being generally in an amount of from about 0.001 to about 10 weight percent by weight of the hair dye composition, preferably from about 0.01 to about 5.0 weight percent. Other couplers, when present, are typically present in an amount such that in aggregate the concentration of couplers in the composition is from about 0.002 to about 10 weight percent, preferably from about 0.01 to about 5.0 weight percent. Other primary intermediates when present are present in an effective dyeing concentration, generally an amount of from about 0.001 to about 10.0 weight percent by weight of the hair dye composition, preferably from about 0.01 to about 5.0 weight percent. The remainder of the hair dye composition comprises a carrier or vehicle for the couplers and primary intermediates, and may comprise various adjuvants as described below.

D. Suitable Carrier

Any suitable carrier or vehicle, generally an aqueous or hydroalcoholic solution, can be employed, preferably an aqueous solution. The carrier or vehicle will generally comprise more than 80 weight percent of the hair dye composition, typically 90 to 99 weight percent, preferably 94 to 99 weight percent. The hair coloring compositions of this invention may contain as adjuvants one or more cationic, anionic, amphoteric, or zwitterionic surface active agents, perfumes, antioxidants such as ascorbic acid, thioglycolic acid or sodium sulfite, chelating and sequestering agents such as EDTA, thickening agents, alkalizing or acidifying agents, solvents, diluents, inerts, dispersing agents, penetrating agents, defoamers, enzymes, and other dye agents (e.g., synthetic direct and natural dyes). These adjuvants are cosmetic additive ingredients commonly used in compositions for coloring hair.

The hair dye compositions of the present invention are used by admixing them with a suitable oxidant, which reacts with the hair dye precursors to develop the hair dye. Any suitable oxidizing agent can be employed in the hair dye product compositions of this invention, particularly hydrogen peroxide ($H_2O_2$) or precursors therefor. Also suitable are urea peroxide, the alkali metal salts of persulfate, perborate, and percarbonate, especially the sodium salt, and melamine peroxide. The oxidant is usually provided in an aqueous composition generally referred to as the developer composition, which normally is provided as a separate component of the finished hair dye product and present in a separate container. The developer composition may also contain, to the extent compatible, various ingredients needed to form the developer composition, i.e., peroxide stabilizers, foam formers, etc., and may incorporate one or more of the adjuvants referred to above, e.g., surface active agents, thickeners, pH modifiers, etc. Upon mixing the hair coloring composition and the developer composition to form a hair dye product composition, the adjuvants are provided in the hair dye product composition as it is applied to the hair to achieve desired product attributes, e.g., pH, viscosity, rheology, etc.

The form of the hair dye product compositions according to the invention can be, for example, a solution, especially an aqueous or aqueous-alcoholic solution. However, the form that is preferred is a thick liquid, cream, gel or an emulsion whose composition is a mixture of the dye ingredients with the conventional cosmetic additive ingredients suitable for the particular preparation.

E. Additional Components

Suitable conventional cosmetic additive ingredients useful in the hair dye and developer compositions, and hence in the hair dye product compositions of this invention are described below, and may be used to obtain desired characteristics of the hair dye, developer and hair dye product compositions.

Solvents: In addition to water, solvents that can be used are lower alkanols (e.g., ethanol, propanol, isopropanol, benzyl alcohol), and polyols (e.g., carbitols, propylene glycol, hexylene glycol, glycerin). Under suitable processing, higher alcohols, such as C8 to C18 fatty alcohols, especially cetyl alcohol, are suitable organic solvents, provided they are first liquified by melting, typically at low temperature (50 to 80° C.), before incorporation of other, usually lipophilic, materials.

The organic solvents are typically present in the hair dye compositions in an amount of from about 5 to about 30% by weight of the hair dye composition. Water is usually present in an amount of from about 5 to about 90% by weight of the hair dye composition, preferably from about 15 to about 75% by weight and most preferably from about 30 to about 65% by weight.

Surfactants: These materials are from the classes of anionic, cationic, amphoteric (including zwitterionic surfactants) or nonionic surfactant compounds. (Cationic surfactants, generally included as hair conditioning materials, are considered separately below.) Suitable surfactants, other than cationic surfactants, include fatty alcohol sulfates, ethoxylated fatty alcohol sulfates, alkylsulfonates, alkylbenzensulfonates, alkyltrimethylammonium salts, alkylbetaines, ethoxylated fatty alcohols, ethoxylated fatty acids, ethoxylated alkylphenols, block polymers of ethylene and/or propylene glycol, glycerol esters, phosphate esters, fatty acid alkanol amides and ethoxylated fatty acid esters, alkyl sulfates, ethoxylated alkyl sulfates, alkyl glyceryl ether sulfonates, methyl acyl taurates, acyl isethionates, alkyl ethoxy carboxylates, fatty acid mono- and diethanolamides. Especially useful are sodium and ammonium alkyl sulfates, sodium and ammonium ether sulfates having 1 to 3 ethylene oxide groups, and nonionic surfactants sold as Tergitols, e.g., C11-C15 Pareth-9, and Neodols, e.g., C12-C15 Pareth-3. They are included for various reasons, e.g., to assist in thickening, for forming emulsions, to help in wetting hair during application of the hair dye product composition, etc. Amphoteric surfactants include, for example, the asparagine derivatives as well betaines, sultaines, glycinates and propionates having an alkyl or alkylamido group of from about 10 to about 20 carbon atoms. Typical amphoteric surfactants suitable for use in this invention include lauryl betaine, lauroamphoglycinate, lauroamphopropionate, lauryl sultaine, myristamidopropyl betaine, myristyl betaine, stearoamphopropylsulfonate, cocamidoethyl betaine, cocamidopropyl betaine, cocoamphoglycinate, cocoamphocarboxypropionate, cocoamphocarboxyglycinate, cocobetaine, and cocoamphopropionate.

The amount of surfactants in the hair dye compositions is normally from about 0.1% to 30% by weight, preferably 1% to 15% by weight.

Thickeners: Suitable thickeners include such as higher fatty alcohols, starches, cellulose derivatives, petrolatum, paraffin oil, fatty acids and anionic and nonionic polymeric thickeners based on polyacrylic and polyurethane polymers. Examples are hydroxyethyl cellulose, hydroxymethylcellulose and other cellulose derivatives, hydrophobically modified anionic polymers and nonionic polymers, particularly such polymers having both hydrophilic and hydrophobic moieties (i.e., amphiphilic polymers). Useful nonionic polymers include polyurethane derivatives such as PEG-150/stearyl alcohol/SDMI copolymer. Suitable polyether urethanes are Aculyn® 22, Aculyn® 44, and Aculyn® 46 polymers sold by Rohm & Haas. Other useful amphiphilic polymers are disclosed in U.S. Pat. No. 6,010,541. Examples of anionic polymers that can be used as thickeners are acrylates copolymer, acrylates/ceteth-20 methacrylates copolymer, acrylates/ceteth-20 itaconate copolymer, and acrylates/beheneth-25 acrylates copolymers. In the case of the associative type of thickeners, e.g., Aculyns 22, 44 and 46, the polymer may be included in one of either the hair dye composition or the developer composition of the hair dye product and the surfactant material in the other. Thus, upon mixing of the hair dye and developer compositions, the requisite viscosity is obtained. The thickeners are provided in an amount to provide a suitably thick product as it is applied to the hair. Such products generally have a viscosity of from 1000 to 100000 cps, and often have a thixotropic rheology.

pH Modifying agents: Suitable materials that are used to adjust pH of the hair dye compositions include alkalizers such alkali metal and ammonium hydroxides and carbonates, especially sodium hydroxide and ammonium carbonate, ammonia, organic amines including methylethanolamine, aminomethylpropanol, mono-, di-, and triethanolamine, and acidulents such as inorganic and inorganic acids, for example phosphoric acid, acetic acid, ascorbic acid, citric acid or tartaric acid, hydrochloric acid, etc. See U.S. Pat. No. 6,027,538.

Conditioners: Suitable conditioning materials include silicones and silicone derivatives; hydrocarbon oils; monomeric quaternary compounds, and quaternized polymers. Monomeric quaternary compounds are typically cationic compounds, but may also include betaines and other amphoteric and zwitterionic materials that provide a conditioning effect. Suitable monomeric quaternary compounds include behentrialkonium chloride, behentrimonium chloride, benzalkonium bromide or chloride, benzyl triethyl ammonium chloride, bis-hydroxyethyl tallowmonium chloride, C12-18 dialkyldimonium chloride, cetalkonium chloride, ceteartrimonium bromide and chloride, cetrimonium bromide, chloride and methosulfate, cetylpyridonium chloride, cocamidoproypl ethyldimonium ethosulfate, cocamidopropyl ethosulfate, cocoethyldimonium ethosulfate, cocotrimonium chloride and ethosulfate, dibehenyl dimonium chloride, dicetyldimonium chloride, dicocodimonium chloride, dilauryl dimonium chloride, disoydimonium chloride, ditallowdimonium chloride, hydrogenated tallow trimonium chloride, hydroxyethyl cetyl dimonium chloride, myristalkonium chloride, olealkonium chloride, soyethomonium ethosulfate, soytrimonium chloride, stearalkonium chloride, and many other compounds. See WO 98/27941. Quaternized polymers are typically cationic polymers, but may also include amphoteric and zwitterionic polymers. Useful polymers are exemplified by polyquaternium-4, polyquaternium-6, polyquaternium-7, polyquaternium-8, polyquaternium-9, polyquaternium-10, polyquaternium-22, polyquaternium-32, polyquaternium-39, polyquaternium-44 and polyquaternium-47. Silicones suitable to condition hair are dimethicone, amodimethicone, dimethicone copolyol and dimethiconol. See also WO 99/34770, published Jul. 15, 1999, for suitable silicones. Suitable hydrocarbon oils would include mineral oil.

Conditioners are usually present in the hair dye composition in an amount of from about 0.01 to about 5% by weight of the composition.

Direct Dyes: The hair dyeing compositions according to the invention can also contain compatible direct dyes including Disperse Black 9, HC Yellow 2, HC Yellow 4, HC Yellow 15, 4-nitro-o-phenylenediamine, 2-amino-6-chloro-4-nitrophenol, HC Red 3, Disperse Violet 1, HC Blue 2, Disperse Blue 3, and Disperse Blue 377. These direct dyes can be contained in the hair coloring compositions of the invention in an amount of from about 0.05 to 4.0 percent by weight.

Natural ingredients: For example, proteins and protein derivatives, and plant materials such as aloe, chamomile and henna extracts.

Carbonate Ion Source and Radical Scavenger System: The hair dyeing compositions may comprise a system comprising a source of carbonate ions, carbamate ions, hydrocarbonate ions, and mixtures thereof, and a radical scavenger, in a sufficient amount to reduce damage to the hair during the coloring process. Typically, such an amount will range from 0.1% to 15%, preferably 0.1% to 10%, more preferably 1% to 7%, by weight of the composition, of the carbonate ion, and from 0.1% to 10%, preferably from 1% to 7%, by weight of the composition, of radical scavenger. Preferably, the radical scavenger is present at an amount such that the ratio of radical scavenger to carbonate ion is from 1:1 to 1:4. The radical scavenger is preferably selected such that it is not an identical species as the alkalizing agent.

Suitable sources for the ions include but are not limited to: sodium carbonate, sodium hydrogen carbonate, potassium carbonate, potassium hydrogen carbonate, guanidine carbonate, guanidine hydrogen carbonate, lithium carbonate, calcium carbonate, magnesium carbonate, barium carbonate, ammonium carbonate, ammonium hydrogen carbonate and mixtures thereof. Preferred sources of carbonate ions are sodium hydrogen carbonate and potassium hydrogen carbonate. Also preferred are ammonium carbonate, and ammonium hydrogen carbonate.

The radical scavenger is a species that can react with a carbonate radical to convert the carbonate radical by a series of fast reactions to a less reactive species. Preferably, when the radical scavenger comprises a nitrogen atom, it has a pKa>7 to prevent the protonation of the nitrogen. Preferred radical scavengers may be selected from the classes of alkanolamines, amino sugars, amino acids and mixtures thereof, and may include, but are not limited to: monoethanolamine, 3-amino-1-propanol, 4-amino-1-butanol, 5-amino-1-pentanol, 1-amino-2-propanol, 1-amino-2-butanol, 1-amino-2-pentanol, 1-amino-3-pentanol, 1-amino-4-pentanol, 3-amino-2-methylpropan-1-ol, 1-amino-2-methylpropan-2-ol, 3-aminopropane-1,2-diol, glucosamine, N-acetylglucosamine, glycine, arginine, lysine, proline, glutamine, histidine, serine, tryptophan and potassium, sodium and ammonium salts of the above and mixtures thereof. Other preferred radical scavenger compounds include benzylamine, glutamic acid, imidazole, di-tert-butylhydroxytoluene, hydroquinone, catechol and mixtures thereof.

Other adjuvants include polysaccharides, alkylpolyglycosides, buffers, chelating and sequestrant agents, antioxidants, and peroxide stabilizing agents, such as those mentioned in WO 01/62221.

The adjuvants referred to above but not specifically identified that are suitable are listed in the International Cosmetics Ingredient Dictionary and Handbook, (Eighth Edition) published by The Cosmetics, Toiletry, and Fragrance Association. In particular reference is made to Volume 2, Section 3 (Chemical Classes) and Section 4 (Functions) are useful in identifying a specific adjuvant to achieve a particular purpose or multipurpose.

The above-mentioned conventional cosmetic ingredients are used in amounts suitable for their functional purposes. For example, the surfactants used as wetting agents, associative agents, and emulsifiers are generally present in concentrations of from about 0.1 to 30 percent by weight, the thickeners are useful in an amount of from about 0.1 to 25 percent by weight, and the hair care functional materials are typically used in concentrations of from about 0.01 to 5.0 percent by weight.

The hair dyeing product composition as it is applied to the hair, i.e., after mixing the hair dye composition according to the invention and the developer, can be weakly acidic, neutral or alkaline according to their composition. The hair dye compositions can have pH values of from about 6 to 11.5, preferably from about 6.8 to about 10, and especially from about 8 to about 10. The pH of the developer composition is typically acidic, and generally the pH is from about 2.5 to about 6.5, usually about 3 to 5. The pH of the hair dye and developer compositions is adjusted using a pH modifier as mentioned above.

F. Method of Use

In order to use the hair coloring composition for dyeing hair, the above-described hair coloring compositions according to the invention are mixed with an oxidizing agent immediately prior to use and a sufficient amount of the mixture is applied to the hair, according to the hair abundance, generally from about 60 to 200 grams. Some of the adjuvants listed above (e.g., thickeners, conditioners, etc.) can be provided in the dye composition or the developer, or both, depending on the nature of the ingredients, possible interactions, etc., as is well known in the art.

Typically, hydrogen peroxide, or its addition compounds with urea, melamine, sodium borate or sodium carbonate, can be used in the form of a 3 to 12 percent, preferably 6 percent, aqueous solution as the oxidizing agent for developing the hair dye. If a 6 percent hydrogen peroxide solution is used as oxidizing agent, the weight ratio of hair coloring composition to the developer composition is 5:1 to 1:5, but preferably 1:1.

In general, the hair dyeing composition comprising primary intermediate(s) and coupler(s) is prepared and at the time of use is admixed with the developer composition containing the oxidizing agent to obtain an essentially homogenous, preferably thickened, composition (the hair dye product composition). Upon such preparation the hair dye product composition is applied to the hair to be dyed and remains in contact with the hair for an amount of time effective to dye the hair. The hair dye product composition is allowed to act on the hair for about 2 to about 60 minutes, preferably about 15 to 45, especially about 30 minutes, at about 15 to 50° C. Thereafter, the hair is rinsed with water, to remove the hair dye product composition and dried. If necessary, the hair is washed with a shampoo and rinsed, e.g., with water or a weakly acidic solution, such as a citric acid or tartaric acid solution, and dried. Optionally, a separate conditioning product may also be provided.

G. Hair Dyeing Product Kit

Together, the hair dye composition and the developer composition form a system for dyeing hair. This system may be provided as a kit comprising in a single package separate containers of the hair dye composition, the developer, the optional conditioner or other hair treatment product, and instructions for use.

H. Non-Limiting Examples

Especially useful primary intermediate and coupler combinations of this invention will provide coloring compositions having outstanding color fastness, fastness to washing, fastness to rubbing, and good selectivity.

When N-phenyl-benzene-1,3-diamine couples with 2-(4,5-diamino-pyrazole-1-yl)-ethanol to color Piedmont hair the hair is colored purple, and when N-(4-Amino-phenyl)-pyridine-2,6-diamine couples with 2-(4,5-diamino-pyrazole-1-yl)-ethanol to color Piedmont hair the hair is colored blue, whereas coupling of N-methyl-benzene-1,3-diamine or benzene-1,3-diamine with the same pyrazole primary intermediate dyes the hair dark red and red, respectively.

The advantageous properties of the hair-coloring compositions of this invention compared to closely related hair coloring composition are illustrated by the following tests.

DYEING EXAMPLE 1

The following composition shown in Table 1 can be used for dyeing Piedmont hair. 100 g of the dyeing composition is mixed with 100 g 20 volume hydrogen peroxide. The resulting mixture is applied to the hair and permitted to remain in contact with the hair for 30 minutes. The dyed hair is then shampooed, rinsed with water and dried. The ranges of ingredients set out in Table 1 are illustrative of useful concentrations of the recited materials in a hair dye product.

TABLE 1

Composition for Dyeing Hair

| Ingredients | Range (wt %) | Weight (%) |
| --- | --- | --- |
| Cocamidopropyl betaine | 0-25 | 17.00 |
| Polyquaternium-22 | 0-7 | 5.00 |
| Monoethanolamine[1] | 0-15 | 2.00 |
| Oleic Acid | 2-22 | 0.75 |
| Citric Acid | 0-3 | 0.10 |
| 28% Ammonium hydroxide[1] | 0-15 | 5.00 |
| Behentrimonium chloride | 1-5 | 0.50 |
| Sodium sulfite | 0-1 | 0.10 |
| EDTA | 0-1 | 0.10 |
| Erythorbic acid | 0-1 | 0.40 |
| Ethoxydiglycol | 1-10 | 3.50 |
| C11-15 Pareth-9 (Tergitol 15-S-9) | 0.5-5 | 1.00 |
| C12-15 Pareth-3 (Neodol 25-3) | 0.25-5 | 0.50 |
| Isopropanol | 2-10 | 4.00 |
| Propylene glycol | 1-12 | 2.00 |
| p-Phenylenediamine | 0-5 | 2 mmoles |
| N,N-Bis(hydroxyethyl)-p-phenylene diamine | 0-5 | 2 mmoles |
| 3-Methyl-p-aminophenol | 0-5 | 1 mmoles |
| p-Aminophenol | 0-5 | 1 mmoles |

TABLE 1-continued

Composition for Dyeing Hair

| Ingredients | Range (wt %) | Weight (%) |
|---|---|---|
| Primary intermediate of this invention | 0.5-5 | 3 mmoles |
| Coupler of this invention | 0.5-5 | 3 mmoles |
| 5-Amino-2-Methyl Phenol | 0-5 | 3 mmoles |
| 2,4-Diaminophenoxyethanol | 0-5 | 3 mmoles |
| m-Phenylenediamine | 0-5 | 1 mmoles |
| Water | qs to 100.00 | qs to 100.00 |

[1] In the aggregate, these ingredients are in the range of 2 to 15% by weight.

DYEING EXAMPLE 2

Piedmont hair weighing from 700 to 900 mg was used. The following compositions A (of this invention), B (comparative), C (comparative), and D (of this invention) shown in Table 2 were used for dyeing Piedmont hair. 10 g of hair dyeing composition was mixed with 100 g of 20 volume hydrogen peroxide. The resulting mixture was applied to the hair and permitted to remain in contact with hair for 30 minutes at about 20° C. Thus dyed hair was then shampooed and rinsed with water and dried. Minolta spectrophotometer CM-3700d from Minolta Co. is used. Color space is CIE L*a*b* and illuminant is D65 daylight with 10° observer. The color space L* indicates lightness and a* and b* are the chromaticity coordinates. +a is the red direction, -a is the green direction, +b is the yellow direction, and -b is the blue direction. Overall color change is represented by ΔE where ΔE is defined by the following formula:

$$\Delta E = \sqrt{(\Delta L^*)^2 + (\Delta a^*)^2 + (\Delta b^*)^2}$$

Acid Perspiration Test Procedure

A dyed tress was placed in a jar containing 60 ml of acid perspiration solution described below and left for 18 h at 40° C. The tress was then rinsed, dried, and measured by Minolta CM-3700d to obtain CIE L*a*b*. The process was repeated under the same conditions in a freshly prepared solution for another 18 h and the tress was again rinsed, dried, and measured.

Acid Perspiration solution consists of 10 g sodium chloride, 1 g lactic acid (USP 85%), 1 g anhydrous disodium hydrogen phosphate ($Na_2HPO_4$) and 0.25 g (+) histidine monohydrochloride in 1 L distilled water.

TABLE 2

Hair Dye Composition

| | A (%) | B (%) | C (%) | D (%) |
|---|---|---|---|---|
| Cocamidopropyl betaine | 17.00 | 17.00 | 17.00 | 17.00 |
| Ethanolamine | 2 | 2 | 2 | 2 |
| Oleic Acid | 0.75 | 0.75 | 0.75 | 0.75 |
| Citric Acid | 0.1 | 0.1 | 0.1 | 0.1 |
| Ammonium hydroxide | 5.0 | 5.0 | 5.0 | 5.0 |
| Behentrimonium chloride | 0.5 | 0.5 | 0.5 | 0.5 |
| Sodium sulfite | 0.1 | 0.1 | 0.1 | 0.1 |
| EDTA | 0.1 | 0.1 | 0.1 | 0.1 |
| Erythorbic acid | 0.4 | 0.4 | 0.4 | 0.4 |
| N-(2-Hydroxyethyl)-4,5-diaminopyrazole sulfate | 0.24 | 0.24 | 0.24 | 0.24 |
| N-Phenyl-benzene-1,3-diamine | 0.461 | | | |
| N-Methyl-benzene-1,3-diamine | | 0.305 | | |
| Benzene-1,3-diamine | | | 0.27 | |
| N-(4-Amino-phenyl)-pyridine-2,6-diamine | | | | 0.80 |
| Water | QS 100 | QS 100 | QS 100 | QS 100 |
| Shade on Piedmont hair | Purple | Dark Red | Red | Blue |

TABLE 3

The CIE L*a*b* values obtained from Compositions A, B, C, and D

| | Before acid perspiration | | | After acid perspiration | | | |
|---|---|---|---|---|---|---|---|
| Composition | L* | a* | b* | L* | a* | b* | ΔE |
| A | 34.03 | 17.73 | -16.75 | 39.00 | 16.96 | -13.94 | 5.76 |
| B | 25.42 | 28.52 | -3.49 | 48.97 | 19.05 | 1.47 | 25.87 |
| C | 27.53 | 32.42 | -4.93 | 48.01 | 23.12 | -0.45 | 22.93 |
| D | 19.72 | 3.00 | -10.89 | 19.82 | 1.48 | -7.11 | 4.08 |

It is notable that N-phenyl-benzene-1,3-diamine couples with 2-(4,5-diamino-pyrazol-1-yl)-ethanol to color the Piedmont hair purple (Composition A), while coupling of N-methyl-benzene-1,3-diamine (Composition B) or benzene-1,3-diamine (Composition C) with the same pyrazole primary intermediate dyes the hair dark red and red, respectively. Additionally, the -b* value of Composition A is -16.75 in contrast to -b* values of -3.49 and -4.93 for Compositions B and C, respectively.

Per Table 3, the fastness of the dyed hair to the effect of acid perspiration shows that Composition A containing N-phenyl-benzene-1,3-diamine exhibits much better color fastness than Composition B containing N-methyl-benzene-1,3-diamine or Composition C containing benzene-1,3-diamine. After 36 hours testing, the total color difference (ΔE) of Composition A is only 5.76, whereas the ΔE for Composition B and Composition C is 25.87 and 22.93, respectively.

It also is notable that N-(4-Amino-phenyl)-pyridine-2,6-diamine couples with 2-(4,5-diamino-pyrazol-1-yl)-ethanol to color the Piedmont hair blue (Composition D), whereas Composition B and Composition C, as discussed above, dye the hair dark red and red, respectively. For Composition D, the -b* value is -10.89, in contrast to -b* values of -3.49 and -4.93 for Compositions B and C, respectively.

Again per Table 3, the fastness of the dyed hair to the effect of acid perspiration shows that Composition D containing N-(4-Amino-phenyl)-pyridine-2,6-diamine exhibits much better color fastness than Composition B or Composition C. After 36 hours testing, the total color difference (ΔE) of Composition D is only 4.08, whereas, as discussed above, the ΔE for Composition B and Composition C is 25.87 and 22.93, respectively.

Accordingly, the hair dyeing compositions of the present invention demonstrate advantageous properties with respect to fastness to acid perspiration compared to closely related hair coloring composition.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A hair dyeing composition comprising:

a) at least one coupler selected from the group consisting of compounds according to the following formula (1), formula (1-B), and formula (1-C):

formula (1)

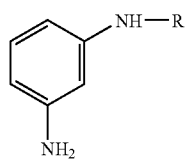
(1)

wherein R is a moiety selected from the following formulae (2), (3) or (4):

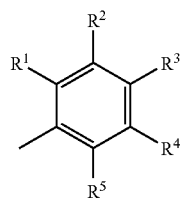
(2)

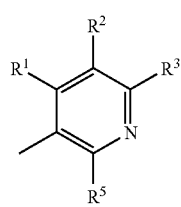
(3)

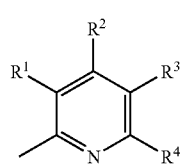
(4)

wherein $R^1$, $R^2$, $R^3$, $R^4$ and $R^5$ are each independently selected from the group consisting of hydrogen, halo, hydroxyl, amino, $C_1$-$C_4$ alkyl or haloalkyl, $C_1$-$C_4$ alkoxy or haloalkoxy, and nitrile;

formula (1-B)

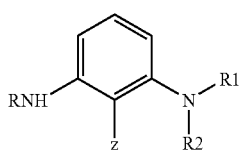
(1-B)

wherein $R^1$ is an aryl ring selected from the group consisting of phenyl and a 5- or 6-membered heteroaryl having one or more heteroatom selected from O, S, or N, wherein said aryl ring is unsubstituted or substituted with one or more substituents selected from the group consisting of hydrogen, halo, hydroxyl, amino, $C_1$-$C_4$ alkyl or haloalkyl, $C_1$-$C_4$ alkoxy or haloalkoxy, and nitrile;

wherein R and $R^2$ are each independently selected from the group consisting of hydrogen, $C_1$-$C_5$ alkyl, $C_1$-$C_5$ monohydroxyalkyl, and $C_2$-$C_5$ dihydroxyalkyl; and wherein Z is selected from the group consisting of $C_1$-$C_5$ alkyl, $C_1$-$C_5$ monohydroxyalkyl, $C_2$-$C_5$ dihydroxyalkyl, $C_1$-$C_5$ aminoalkyl, and $C_1$-$C_5$ methoxyalkyl; and formula (1-C)

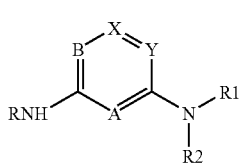
(1-C)

wherein $R^1$ is an aryl ring selected from the group consisting of phenyl and a 5- or 6-membered heteroaryl having one or more heteroatom selected from O, S, or N, wherein said aryl ring is unsubstituted or substituted with one or more substituents selected from the group consisting of hydrogen, halo, hydroxyl, amino, $C_1$-$C_4$ alkyl or haloalkyl, $C_1$-$C_4$ alkoxy or haloalkoxy, and nitrile;

wherein R and $R^2$ are each independently selected from the group consisting of hydrogen, $C_1$-$C_5$ alkyl, $C_1$-$C_5$ monohydroxyalkyl, and $C_2$-$C_5$ dihydroxyalkyl; and wherein any one of A, B, X, and Y is nitrogen and the remaining of A, B, X, and Y are each carbon;

b) at least one primary intermediate of the formula (5):

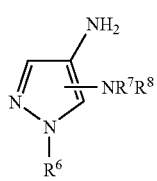
(5)

wherein $R^6$ and $R^7$ are independently selected from the group consisting of hydrogen, $C_1$-$C_4$ alkyl, $C_2$-$C_4$ hydroxyalkyl, benzyl, and phenyl; and wherein $R^8$ is selected from the group consisting of hydrogen, $C_1$-$C_4$ alkyl, and $C_2$-$C_4$ hydroxyalkyl;

or physiologically tolerated, water-soluble salts thereof; and c) a suitable carrier.

2. A hair dyeing composition according to claim 1, wherein said coupler is a compound according to formula (1) and is selected from the group consisting of N-phenyl-benzene-1,3-diamine, N-(4-amino-phenyl)-benzene-1,3-diamine, 4-methoxyphenyl-(3-amino-phenyl)-amine, and 3-methoxyphenyl-(3-amino-phenyl)-amine, and wherein said primary intermediate is 2-(4,5-diamino-pyrazol-1-yl)-ethanol.

3. A hair dyeing composition according to claim 1, wherein said coupler is selected from the group consisting of compounds according to formula (1-B) and compounds according to formula (1-C).

4. A hair dyeing composition according to claim 3, wherein said coupler is a compound according to formula (1-B) and is selected from the group consisting of N2-(3-amino-2-methyl-phenyl)-pyridine-2,5-diamine, N-(4-amino-phenyl)-2-methyl-benzene-1,3-diamine, N-(4-amino-phenyl)-N'-ethyl-2-methyl-benzene-1,3-diamine, 2-[2-amino-6-(4-amino-phenylamino)-phenyl]-ethanol, 2-[[4-(3-amino-2-methyl-phenylamino)-phenyl]-(2-hydroxy-ethyl)-amino]-ethanol, 2-methyl-N-(4-pyrrolidin-1-yl-phenyl)-benzene-1,3-diamine, 2-Aminomethyl-N-(4-amino-phenyl)-benzene-1,3-diamine, [2-amino-6-(4-aminophenylamino)-phenyl]-methanol, N-(4-amino-phenyl)-2-methoxymethyl-benzene-1,3-diamine, N1-[3-amino-2-(aminomethyl)phenyl]benzene-1,4-diamine, N1-[3-amino-2-(cyanomethyl)phenyl]benzene-1,4-diamine, N1-(3-amino-2-vinylphenyl)benzene-1,4-diamine, N1-[3-amino-2-(hydroxymethyl)phenyl]benzene-1,4-diamine, 2-[N-(3-aminophenyl)-N-(4-aminophenyl)amino]ethanol, N1-[3-amino-2-(1-hydroxyethyl)phenyl]benzene-1,4-diamine, N1,N1-bis(2-hydroxyethyl)-N-4-(3'-aminophenyl)-1,4-diaminobenzene, N1-{3-amino-2-[(E)-prop-1-enyl]phenyl}benzene-1,4-diamine, 1-(4-aminophenyl)-1,2,3,4-tetrahydroquinolin-5-amine, 1-(4-aminophenyl)indolin-4-amine, N1-(1,2-dihydroquinolin-5-yl)benzene-1,4-diamine, and N1-(indolin-4-yl)benzene-1,4-diamine, and wherein said primary intermediate is 2-(4,5-diamino-pyrazol-1-yl)-ethanol.

5. A hair dyeing composition according to claim 3, wherein said coupler is a compound according to formula (1-C) and is selected from the group consisting of N-(4-amino-phenyl)-pyridine-2,6-diamine, N-(5-amino-pyridin-2-yl)pyridine-2,6-diamine, N-(5-aminopyridin-2-yl)benzene-1,3-diamine, N-(4-pyrrolidin-1-yl-phenyl)-pyridine-2,6-diamine, N-(4-amino-phenyl)-N'-methyl-pyridine-2,6-diamine, 2-[4-(6-methylamino-pyridin-2-ylamino)-phenylamino]-ethanol, 2-[6-(4-amino-phenylamino)-pyridin-2-ylamino]-ethanol, N-(4-amino-phenyl)-N-methyl-pyridine-2,6-diamine, N-(1H-pyrrol-2-yl)-pyridine-2,6-diamine, N-(6-amino-pyridin-2-yl)-pyrimidine-2,4,5,6-tetraamine, N-(5-amino-[1,3,4]thiadiazol-2-yl)-pyridine-2,6-diamine, N3-(4-aminophenyl)pyridine-3,5-diamine, N3-(4-aminophenyl)-N-5-(2-hydroxyethyl)pyridine-3,5-diamine, N3-(thiazol-2-yl)pyridine-3,5-diamine, N2-(4-aminophenyl)pyridine-2,4-diamine, N2-(4-aminophenyl)-5-chloropyridine-2,6-diamine, N2-(4-aminophenyl)-5-methoxypyridine-2,6-diamine, N3-(4-aminophenyl)-N-3-methylpyridine-3,5-diamine, N3-(5-aminopyridin-2-yl)pyridine-3,5-diamine, N3-(4,5,6-triaminopyrimidin-2-yl)pyridine-3,5-diamine, N2-(4-aminophenyl)-N-2-methylpyridine-2,4-diamine, N4-(4-aminophenyl)-N-4-methylpyridine-2,4-diamine, N2-(4-aminophenyl)-3-chloropyridine-2,6-diamine, and N2-(4-aminophenyl)-3-methoxypyridine-2,6-diamine, and wherein said primary intermediate is 2-(4,5-diamino-pyrazol-1-yl)-ethanol.

6. A hair dyeing composition according to claim 1, further comprising one or more additional components selected from the group consisting of auxiliary couplers, auxiliary primary intermediates, direct dyes, oxidizing agents, thickeners, pH modifying agents, conditioning materials, and carbonate ion source and radical scavenger systems.

7. A method of dyeing hair, said method comprising the steps of:

a) applying to the hair a hair dyeing composition according to claim 1; and b) rinsing the hair with water.

8. A hair dyeing product in kit form comprising:

a) a first separate container of a hair dyeing composition according to claim 1; and b) a second separate container of an oxidizing agent composition.

* * * * *